(12) United States Patent
Lee et al.

(10) Patent No.: US 11,857,292 B2
(45) Date of Patent: Jan. 2, 2024

(54) METHOD FOR DIAGNOSING VASCULAR DISEASE AND APPARATUS THEREFOR

(71) Applicant: E8IGHT Co., Ltd., Seoul (KR)

(72) Inventors: Joon Sang Lee, Seoul (KR); Young Woo Kim, Seoul (KR)

(73) Assignee: E8IGHT Co., Ltd., Seoul (KR)

( * ) Notice: Subject to any disclaimer, the term of this patent is extended or adjusted under 35 U.S.C. 154(b) by 569 days.

(21) Appl. No.: 16/925,010

(22) Filed: Jul. 9, 2020

(65) Prior Publication Data

US 2021/0290077 A1 Sep. 23, 2021

(30) Foreign Application Priority Data

Mar. 18, 2020 (KR) .................. 10-2020-0033345

(51) Int. Cl.
*A61B 5/02* (2006.01)
*A61B 34/10* (2016.01)
(Continued)

(52) U.S. Cl.
CPC .......... *A61B 5/02007* (2013.01); *A61B 5/026* (2013.01); *A61B 5/1075* (2013.01); *A61B 5/7267* (2013.01); *A61B 34/10* (2016.02); *G06F 21/32* (2013.01); *G16H 10/60* (2018.01); *G16H 50/20* (2018.01); *G16H 50/30* (2018.01); *G16H 50/50* (2018.01); *G16H 50/70* (2018.01); *G16H 70/60* (2018.01); *A61B 6/507* (2013.01)

(58) Field of Classification Search
CPC ... A61B 5/02007; A61B 5/026; A61B 5/7267; A61B 34/10; A61B 5/1075; G06F 21/32; G16H 10/60; G16H 50/20; G16H 50/30; G16H 50/50; G16H 50/70; G16H 70/60
See application file for complete search history.

(56) References Cited

U.S. PATENT DOCUMENTS 9,349,178 B1 * 5/2016 Itu .................. A61B 6/507
2008/0242977 A1 10/2008 Sirohey et al.
(Continued)

FOREIGN PATENT DOCUMENTS

KR 1020190018559 A 2/2019
KR 1020190047073 A 5/2019
(Continued)

*Primary Examiner* — Eric F Winakur
*Assistant Examiner* — Emily C Clement
(74) *Attorney, Agent, or Firm* — Dinsmore & Shohl LLP; Yongsok Choi, Esq.

(57) ABSTRACT

Disclosed are a method for diagnosing a vascular disease and an apparatus therefor. A vascular disease diagnosing method according to an exemplary embodiment of the present disclosure includes: an information acquiring step of acquiring patient information for a diagnosis subject; an FFR processing step of applying a geometric feature parameter information generated based on the patient information to a first learning model to calculate fractional flow reserve (FFR) information; a CFD processing step of applying the geometric feature parameter information to computational fluid dynamics (CFD) to calculate flow feature information; and a diagnosing step of determining a vascular disease based on the fractional flow reserve information and the flow feature information and determine whether to perform a surgery on the vascular disease.

8 Claims, 13 Drawing Sheets

(51) Int. Cl.
*G16H 70/60* (2018.01)
*G16H 50/50* (2018.01)
*G16H 50/30* (2018.01)
*G16H 50/70* (2018.01)
*G16H 50/20* (2018.01)
*A61B 5/026* (2006.01)
*A61B 5/00* (2006.01)
*G16H 10/60* (2018.01)
*A61B 5/107* (2006.01)
*G06F 21/32* (2013.01)
*A61B 6/00* (2006.01)

(56) References Cited

U.S. PATENT DOCUMENTS

| | | | |
|---|---|---|---|
| 2012/0041739 A1* | 2/2012 | Taylor | A61B 6/5205 |
| | | | 703/11 |
| 2016/0106321 A1 | 4/2016 | Sharma et al. | |
| 2016/0321417 A1 | 11/2016 | Fonte et al. | |
| 2019/0183579 A1* | 6/2019 | Kosior | A61B 6/032 |
| 2020/0098124 A1* | 3/2020 | Wang | G06T 7/62 |

FOREIGN PATENT DOCUMENTS

| | | | | |
|---|---|---|---|---|
| KR | | 102032611 B1 | 10/2019 | |
| WO | WO-2018057529 A1 * | | 3/2018 | A61B 5/0044 |

* cited by examiner

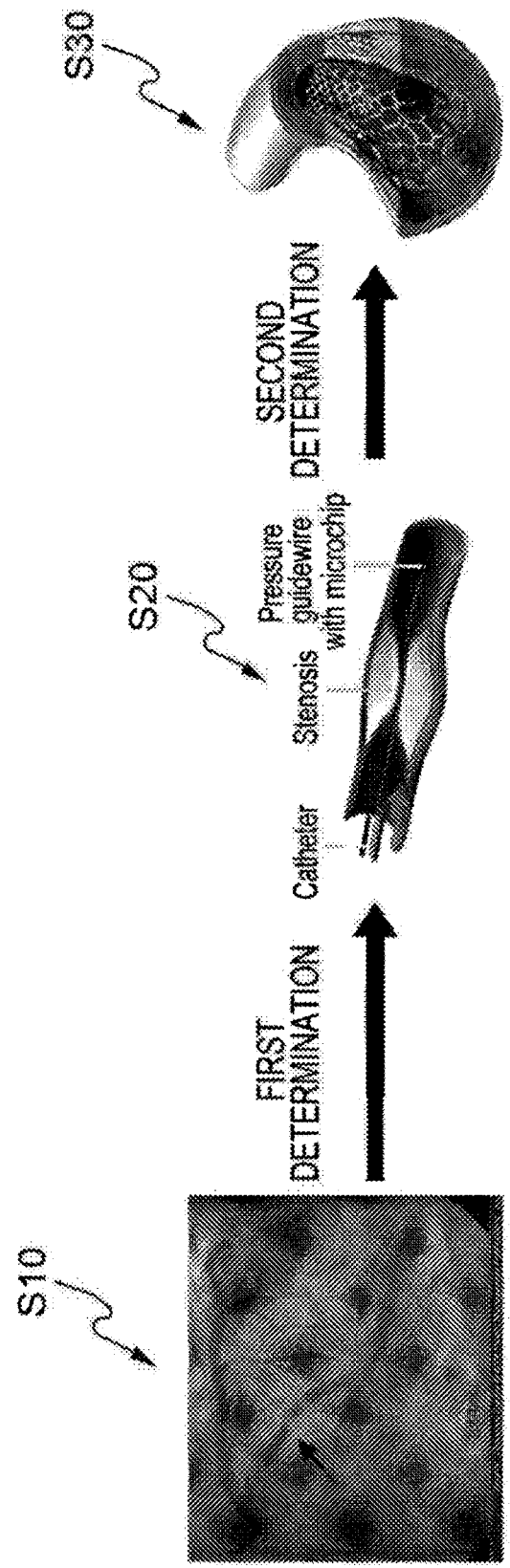
[FIG. 1A]
Prior Art

【FIG. 1B】

|  | $FFR_{EXP}$ | $FFR_{CFD}$ | $FFR_{ML}$ |
|---|---|---|---|
| Method | Invasive | Non-invasive | Non-invasive |
| Cost | High | Medium | Low |
| Time | High | Minimum 3 hours[1] | Less than 1 min |
| Accuracy | 100% | 80%[1] | 80%* |

Prior Art

[FIG. 3]
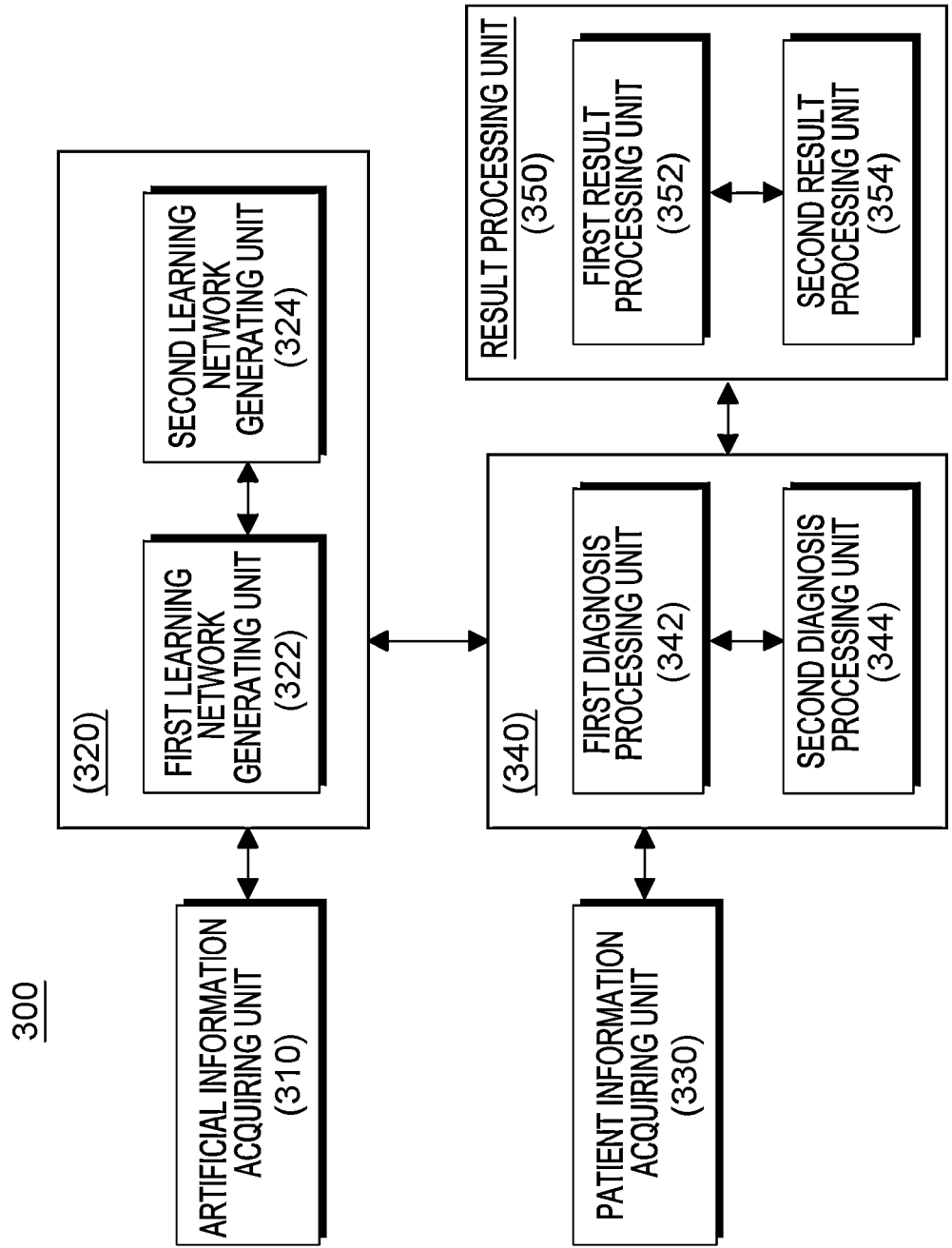

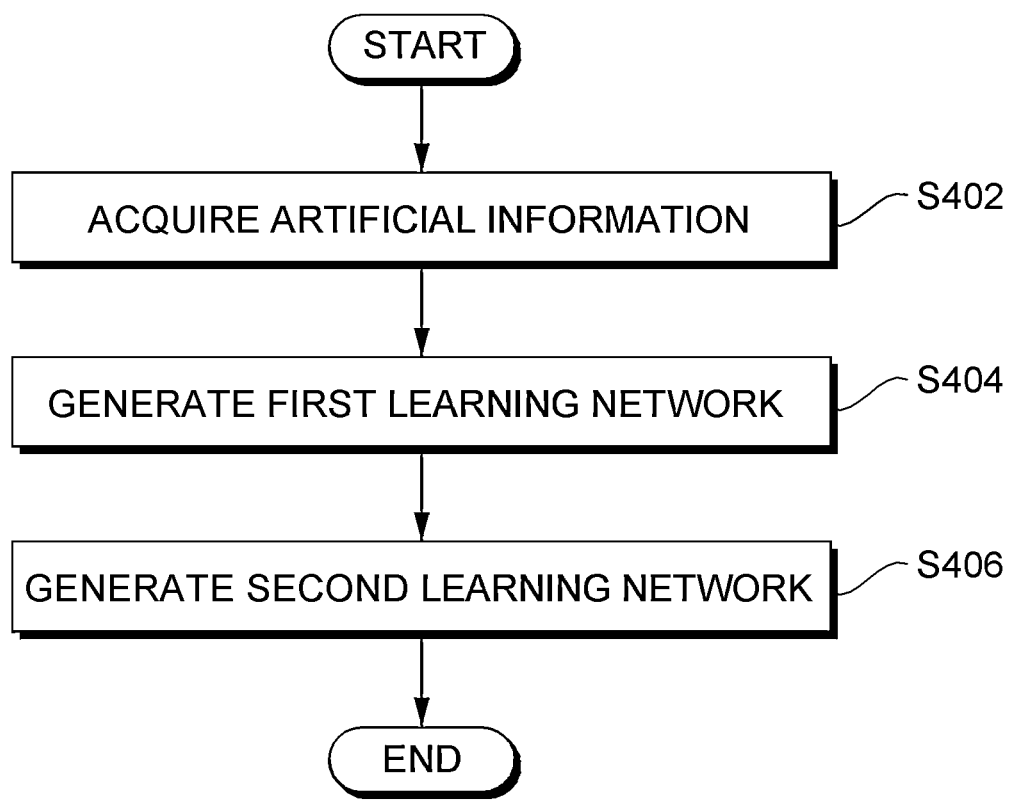
[FIG. 4A]

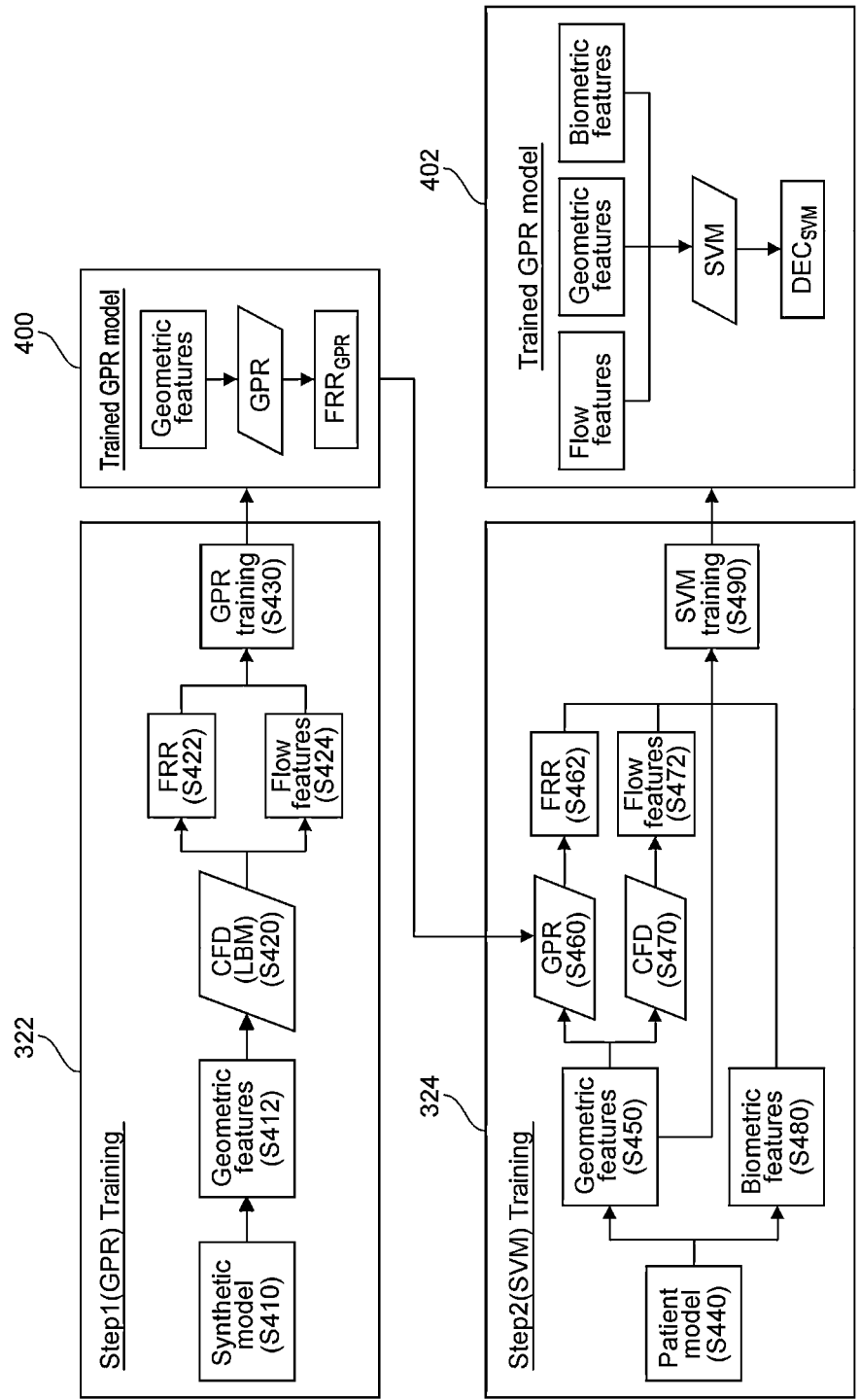

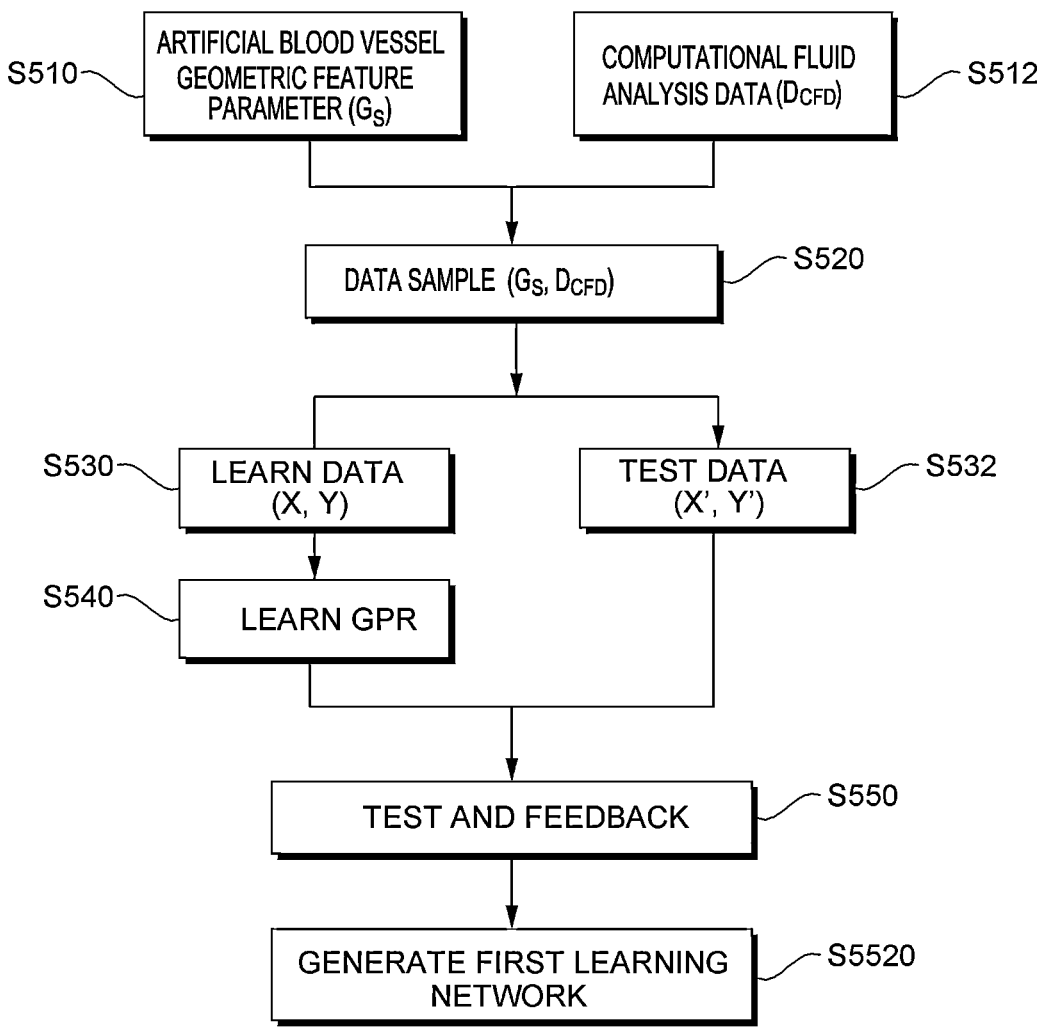
[FIG. 5A]

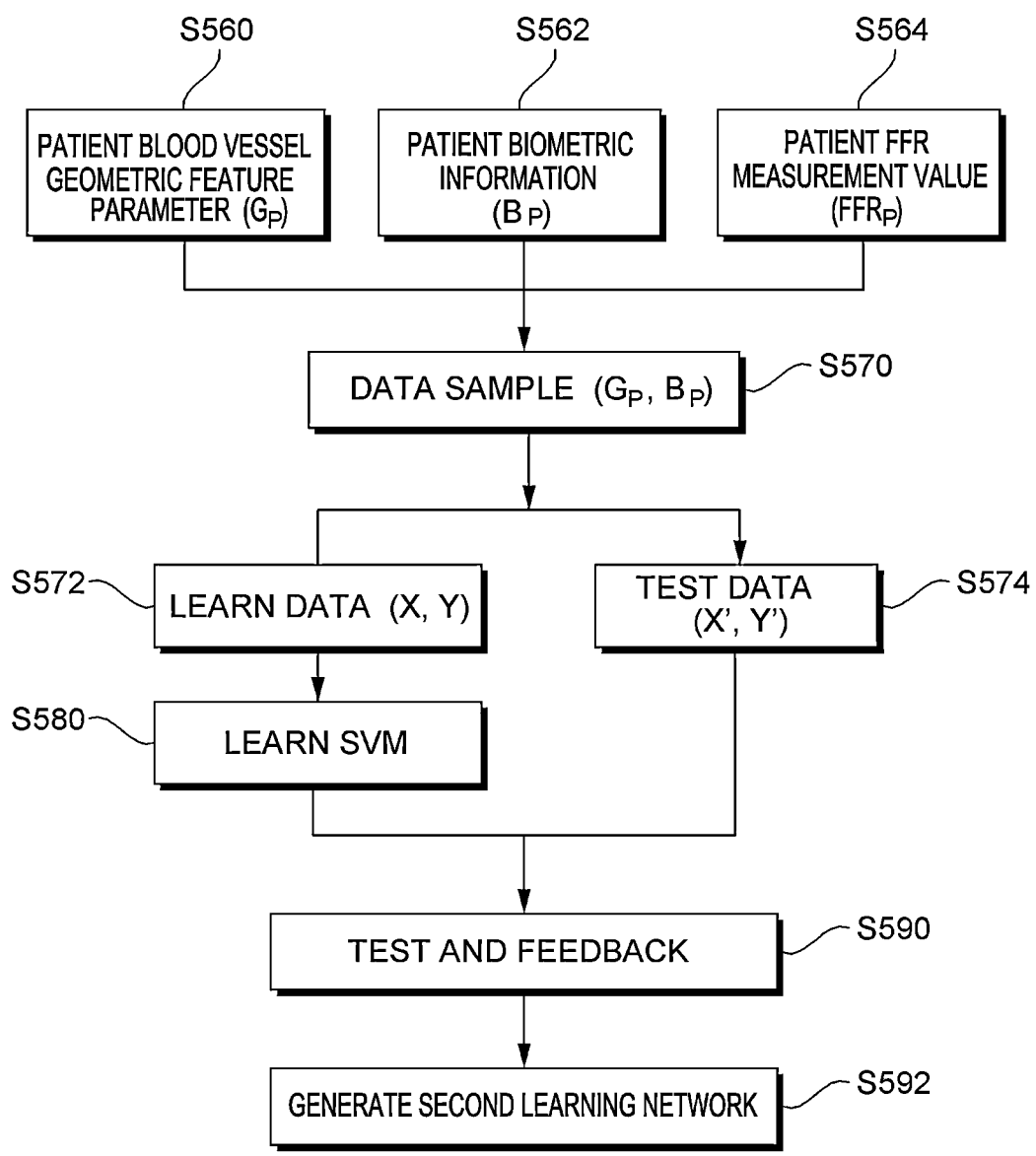

[FIG. 6A]
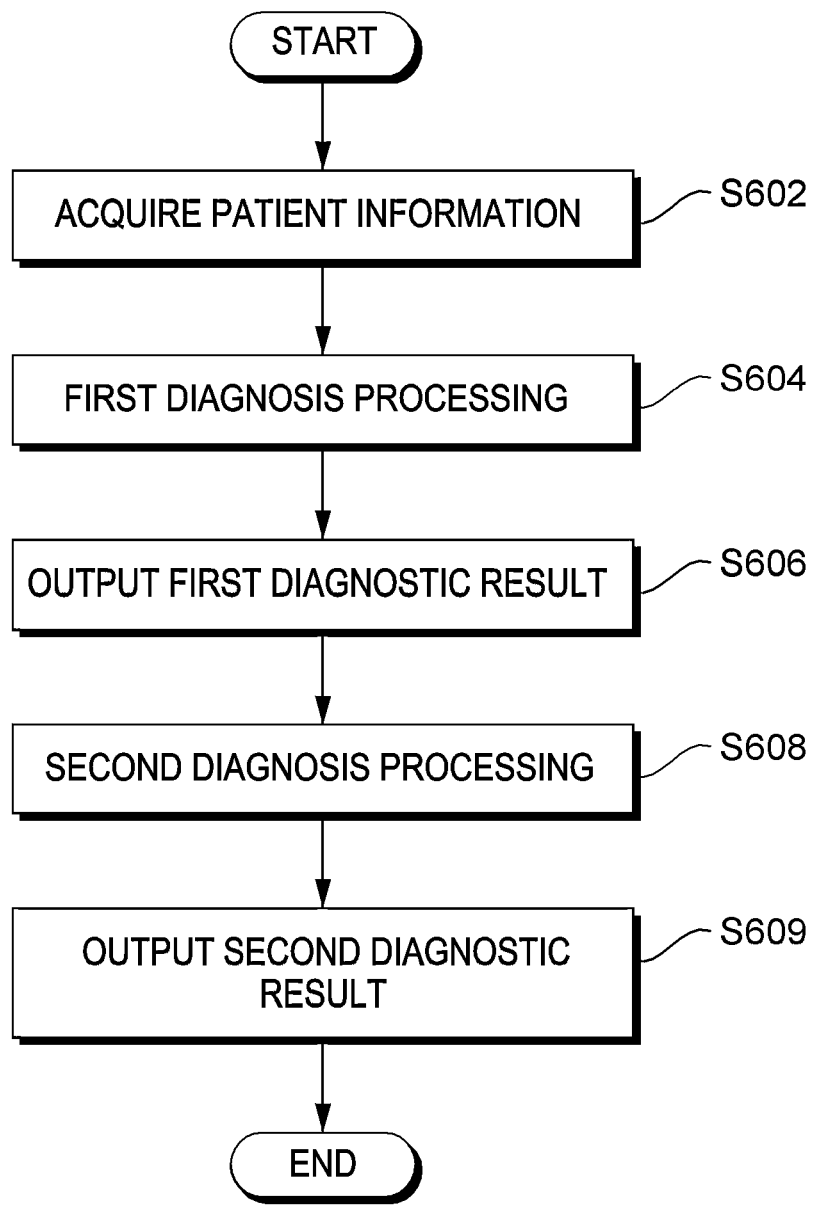

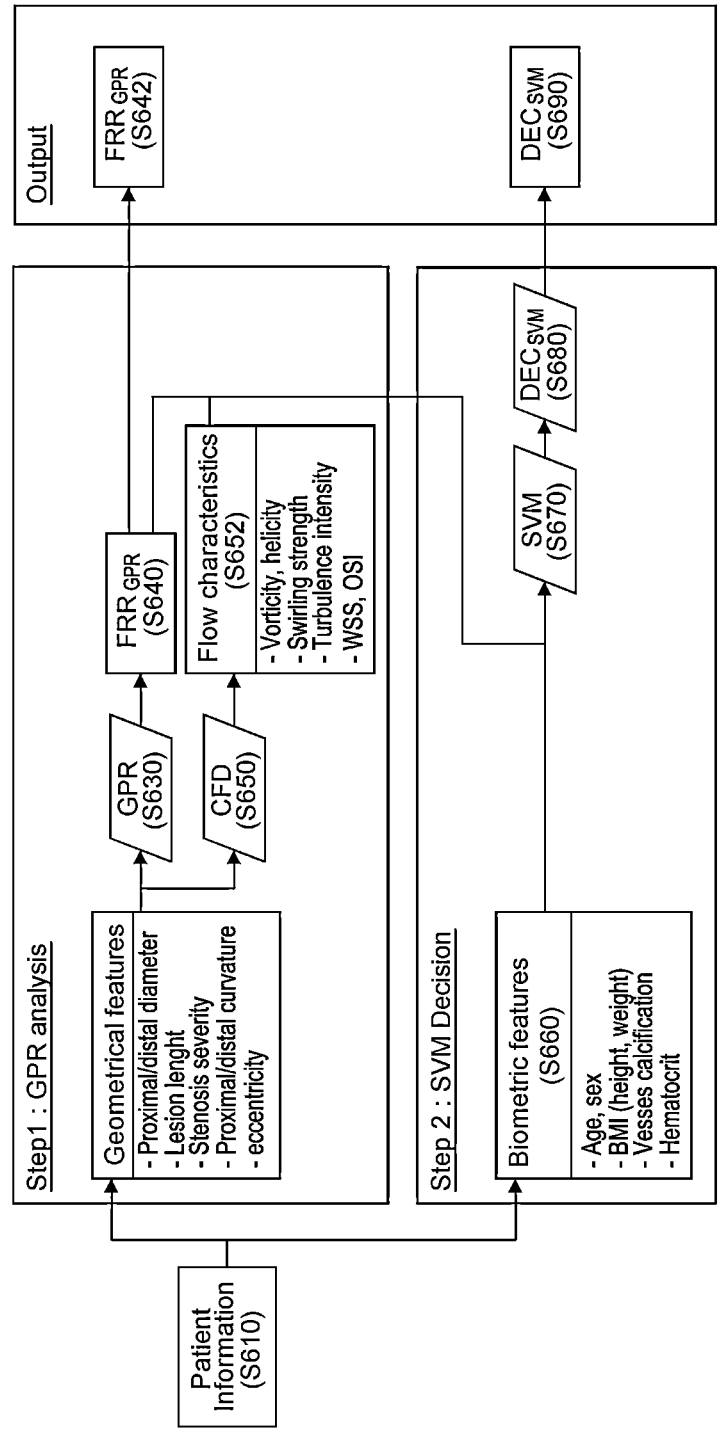
[FIG. 6B]

[FIG. 7A]

| No. | Patient ID | FFR$_{EXP}$ | DEC$_{EXP}$ | FFR$_{CFD}$ | FFR$_{GPR}$ | DEC$_{SVM}$ | Category |
|---|---|---|---|---|---|---|---|
| 1 | F155 | 0.38 | 1 | 0.722 | 0.723 | 1 | 1 (Matched) |
| 2 | F187 | 0.53 | 1 | 0.624 | 0.622 | 1 | |
| 3 | F172 | 0.71 | 1 | 0.767 | 0.773 | 1 | |
| 4 | F200 | 0.78 | 1 | 0.696 | 0.701 | 1 | |
| 5 | F134 | 0.79 | 1 | 0.704 | 0.698 | 1 | |
| 6 | F194 | 0.85 | 0 | 0.842 | 0.838 | 0 | |
| 7 | F87 | 0.86 | 0 | 0.904 | 0.906 | 0 | |
| 8 | F133 | 0.87 | 0 | 0.823 | 0.819 | 0 | |
| 9 | F18 | 0.9 | 0 | 0.901 | 0.901 | 0 | |
| 10 | F176 | 0.91 | 0 | 0.847 | 0.844 | 0 | |
| 11 | F201 | 0.94 | 0 | 0.926 | 0.928 | 0 | |
| 12 | F152 | 0.88 | 0 | 0.752 | 0.745 | 0 | 2 (Only SVM matched) |
| 13 | F188 | 0.88 | 0 | 0.782 | 0.784 | 0 | |
| 14 | F178 | 0.90 | 0 | 0.759 | 0.763 | 0 | |
| 15 | F198 | 0.77 | 1 | 0.789 | 0.8140 | 1 | |
| 16 | F159 | 0.79 | 1 | 0.799 | 0.7942 | 0 | 3 (Only GPR matched) |
| 17 | F163 | 0.78 | 1 | 0.799 | 0.7920 | 0 | |
| 18 | F136 | 0.6 | 1 | 0.86 | 0.8537 | 0 | 4 (Mismatched) |
| 19 | F116 | 0.77 | 1 | 0.829 | 0.8291 | 0 | |
| 20 | F168 | 0.94 | 0 | 0.760 | 0.7512 | 1 | |

[FIG. 7B]

|  | FFR$_{CFD}$ | FFR$_{GPR}$ | DEC$_{CARDIA}$ |
|---|---|---|---|
| accuracy | 65 | 65 | 75 |
| sensitivity | 70 | 70 | 50 |
| specificity | 60 | 60 | 80 |

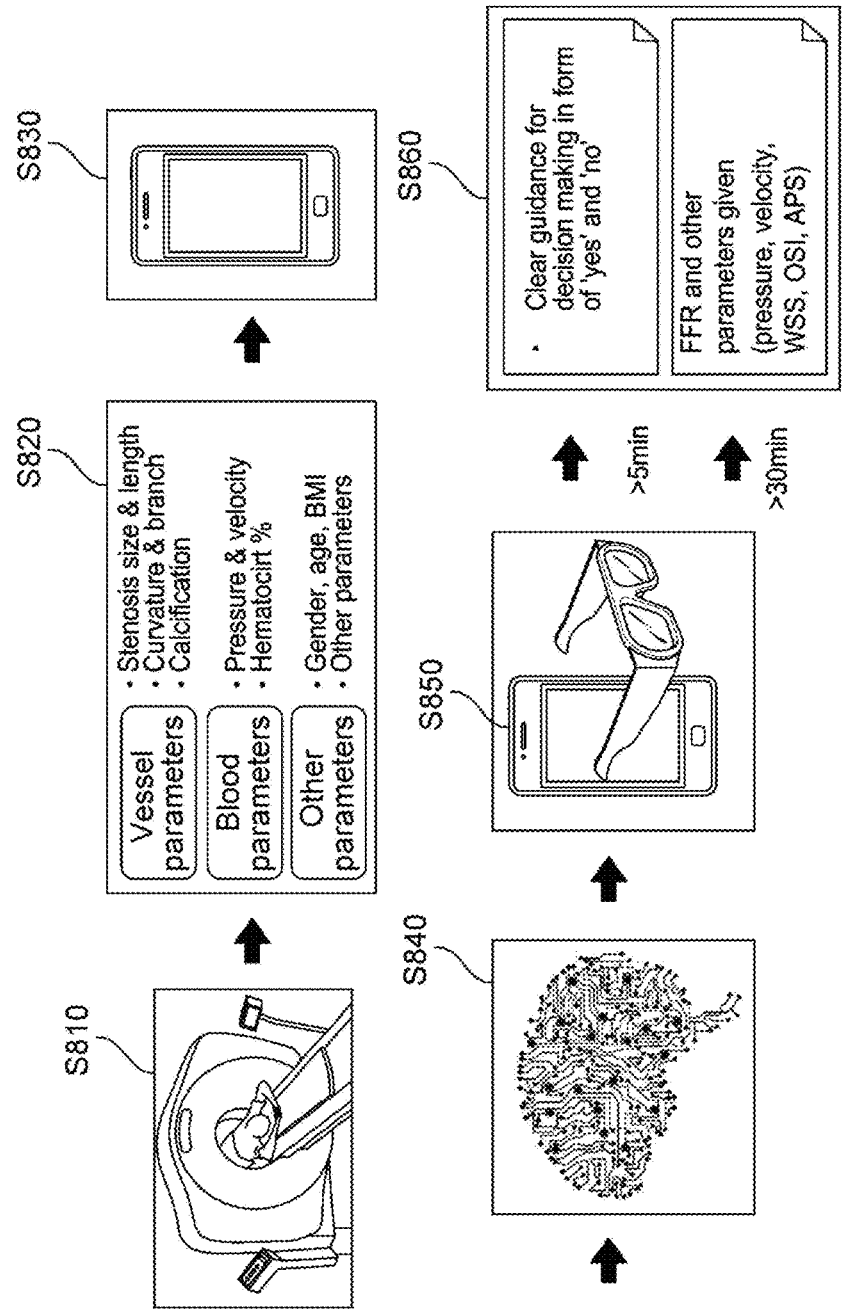
[FIG. 8]

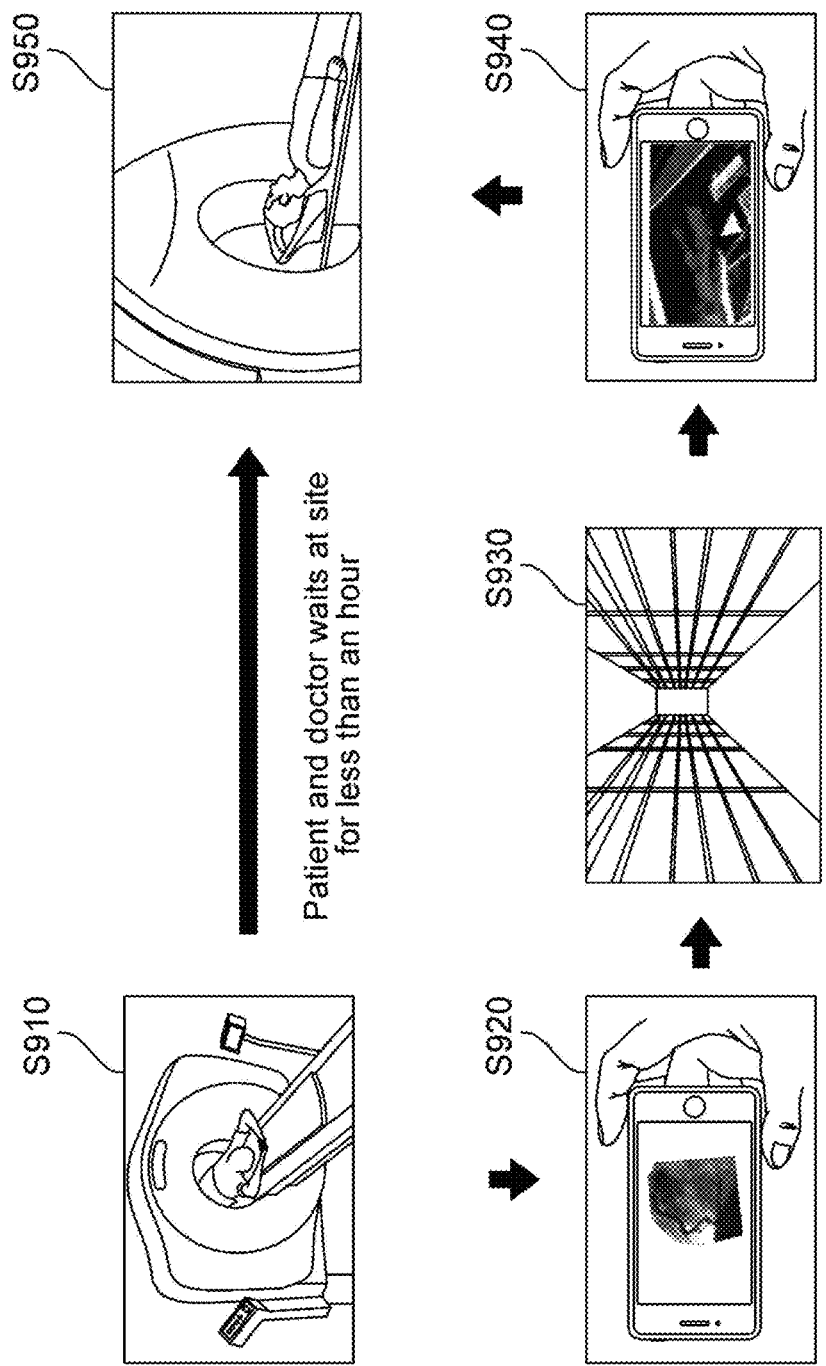

METHOD FOR DIAGNOSING VASCULAR DISEASE AND APPARATUS THEREFOR

CROSS-REFERENCE TO RELATED APPLICATIONS

This application claims priority to and the benefit of Korean Patent Application No. 10-2020-0033345 filed in the Korean Intellectual Property Office on Mar. 18, 2020, the entire contents of which are incorporated herein by reference.

TECHNICAL FIELD

The present disclosure relates to a method for diagnosing a vascular disease of a diagnosis subject and an apparatus therefor.

BACKGROUND ART

The contents described in this section merely provide background information on the exemplary embodiment of the present disclosure, but do not constitute the related art. Plagues maybe formed in blood vessels such as carotid arteries and coronary arteries and stenosis caused by the formed plaques is an important risk factor of stroke or myocardial ischemia. A treatment method maybe determined depending on the state of stenosis (severity). For example, the treatment method maybe determined by one of intervention, stent placement, or drug treatment depending on the state of the stenosis (severity).

Generally, an indicator called fractional flow reserve (FFR) is used for a process for evaluating the severity of stenosis or the likelihood of plaque rupture from the blood vessels.

Doctors who have a lot of experiences in vascular disease may determine the vascular stenosis with naked eye through angioplasty in step S10 of FIG. 1A. In contrast, inexperienced doctors measure the fractional flow reserve (FFR) of the blood vessel in step S20 of FIG. 1A and determine the blood stenosis to determine a treatment method such as stent placement in step S30 of FIG. 1A.

Referring to FIG. 1B, in order to diagnose cardiovascular such as stenosis, the FFR (fractional flow reserve) measuring method ($FFR_{EXP}$) was used to calculate a pressure difference by directly inserting a pressure sensor into the blood vessel. However, this method $FFR_{EXP}$ is invasive and causes issues of time and cost.

In order to solve the problem of $FFR_{EXP}$, a method $FFR_{CFD}$ which predicts the FFR by performing the computational fluid dynamics using a blood vessel image captured by a device such as CT has been utilized. However, this method $FFR_{CFD}$ does not completely replace the existing invasive FFR measuring method $FFR_{EXP}$, but is utilized as an auxiliary means due to the problems such as a calculating time, a computer resource, and accuracy.

Recently, in order to solve the problems of the methods for measuring the fractional flow reserve (FFR), various technologies for a cardiovascular diagnosis method $FFR_{ML}$ using a machine learning technology have been attempted. However, when a general machine learning technique is utilized, a quality and a quantity of data required to learn the algorithm are not sufficient so that it is difficult to construct an algorithm which is clinically applicable.

SUMMARY OF THE INVENTION

The present disclosure relates to a method for diagnosing a vascular disease and an apparatus therefor. Specifically, a main object of the present disclosure is to provide a method for diagnosing a vascular disease which determines a vascular disease by reflecting biometric authentication information of a diagnosis subject to a fractional flow reserve calculated based on geometric feature parameter information generated based on patient information of the diagnosis subject and flow feature information calculated by the computational fluid dynamics and determines whether to perform a surgery for the vascular disease in accordance with the determination result, and an apparatus therefor.

According to an aspect of the present disclosure, in order to achieve the above-described object, a vascular disease diagnosing method includes: an information acquiring step of acquiring patient information for a diagnosis subject; an FFR processing step of applying a geometric feature parameter information generated based on the patient information to a first learning model to calculate fractional flow reserve (FFR) information; a CFD processing step of applying the geometric feature parameter information to computational fluid dynamics (CFD) to calculate flow feature information; and a diagnosing step of determining a vascular disease based on the fractional flow reserve information and the flow feature information and determining whether to perform a surgery on the vascular disease.

According to another aspect of the present disclosure, in order to achieve the above-described object, a vascular disease diagnosing apparatus includes: at least one or more processors; and a memory in which one or more programs executed by the processors are stored, in which when the programs are executed by one or more processors, the programs allow one or more processors to perform operations including: an information acquiring step of acquiring patient information for a diagnosis subject; an FFR processing step of applying a geometric feature parameter information generated based on the patient information to a first learning model to calculate fractional flow reserve (FFR) information; a CFD processing step of applying the geometric feature parameter information to computational fluid dynamics (CFD) to calculate flow feature information; and a diagnosing step of determining a vascular disease based on the fractional flow reserve information and the flow feature information and determining whether to perform a surgery on the vascular disease.

As described above, according to the present disclosure, it is possible to establish a digital environment in which a diagnostician may easily handle the vascular diagnosis in a medial environment.

Further, according to the present disclosure, it is possible to automate the process for diagnosing a vascular disease and minimize a part which needs to be directly performed by a user through a uniform process.

Further, according to the present disclosure, it is possible to quickly and accurately determine whether the surgery is necessary depending on a condition of the diagnosis subject so that a diagnosis cost may be reduced.

BRIEF DESCRIPTION OF THE DRAWINGS

FIGS. 1A and 1B are exemplary diagrams for explaining a vascular disease diagnosing method of the related art;

FIG. 2 is a block diagram schematically illustrating a computing device for diagnosing a vascular disease according to an exemplary embodiment of the present disclosure;

FIG. 3 is a block diagram schematically illustrating a vascular disease diagnosing apparatus according to an exemplary embodiment of the present disclosure;

FIGS. 4A and 4B are flow charts for explaining an operation of generating a learning model for diagnosing a vascular disease according to an exemplary embodiment of the present disclosure;

FIGS. 5A and 5B are flow charts for explaining an operation of generating a first learning model and a second learning model according to an exemplary embodiment of the present disclosure;

FIGS. 6A and 6B are flow charts for explaining a method for diagnosing a vascular disease according to an exemplary embodiment of the present disclosure;

FIG. 7A and 7B are an exemplary view illustrating a diagnostic result of a vascular disease according to an exemplary embodiment of the present disclosure and a diagnostic result of a vascular disease according to the related art; and FIGS. 8 and 9 are exemplary views for explaining an operation of a vascular disease system according to an exemplary embodiment of the present disclosure.

DETAILED DESCRIPTION OF THE EMBODIMENT

Hereinafter, exemplary embodiments of the present disclosure will be described in detail with reference to the accompanying drawings. If it is considered that the description of related known configuration or function may cloud the gist of the present disclosure, the description will be omitted. Further, hereinafter, exemplary embodiments of the present invention will be described. However, it should be understood that the technical spirit of the present disclosure is not limited to the specific embodiments, but may be changed or modified in various ways by those skilled in the art. Hereinafter, a method for diagnosing a vascular disease and an apparatus therefor proposed by the present disclosure will be described in detail with reference to drawings.

A method for diagnosing a vascular disease and an apparatus therefor according to the present disclosure may be desirably a method and an apparatus for diagnosing a cardiovascular disease, specifically, cardiovascular stenosis and determining a treatment method, but are not necessarily limited thereto and may be applied to various blood vessel diseases. FIG. 2 is a block diagram schematically illustrating a computing device for diagnosing a vascular disease according to an exemplary embodiment of the present disclosure.

A computing device 200 for diagnosing a vascular disease according to the present exemplary embodiment includes an input unit 210, an output unit 220, a processor 230, a memory 240, and a database 250. The computing device 200 of FIG. 2 is an example so that all blocks illustrated in FIG. 2 are not essential components and in the other exemplary embodiment, some blocks included in the computing device 200 maybe added, modified, or omitted. In the meantime, the computing device 200 may be implemented as a diagnosing apparatus which diagnoses a vascular disease and each component included in the computing device 200 may be implemented as separate software devices or as a separate hardware device in which the software is combined.

The computing device 200 for diagnosing a vascular disease performs an operation of determining a vascular disease by reflecting biometric authentication information of a diagnosis subject to fractional flow reserve calculated based on geometric feature parameter information generated based on patient information and flow feature information calculated by the computational fluid dynamics and determining whether to perform a surgery for the vascular disease.

The input unit 210 refers to a unit which inputs or acquires a signal or data to perform an operation of diagnosing a vascular disease and determining whether to perform a surgery. The input unit 210 interworks with the processor 230 and inputs various types of signals or data or directly acquires data by interworking with an external device to transmit the signal or data to the processor 230. Here, the input unit 210 may be a device or a server which inputs a synthetic model, a virtual patient model, patient information, various condition information, or a control signal, but is not necessarily limited thereto.

The output unit 220 may interwork with the processor 230 to display various information such as a first diagnostic result and a second diagnostic result. The output unit 220 may desirably display various information through a display (not illustrated) equipped in the computing device 200 for diagnosing a vascular disease, but is not necessarily limited thereto.

The processor 230 performs a function of executing at least one instruction or program included in the memory 240. The processor 230 according to the exemplary embodiment performs an operation of generating a first learning model and a second learning model based on the synthetic model and the virtual patient model acquired from the input unit 210 or a database 250.

Further, the processor 230 according to the exemplary embodiment performs an operation of determining a vascular disease based on patient information for a diagnosis subject acquired from the input unit 210 or the database 250 and determining whether to perform the surgery on the vascular disease.

The memory 240 includes at least one instruction or program which is executable by the processor 230. The memory 240 may include an instruction or a program for generating the first learning model and the second learning model and performing a first diagnosis processing and a second diagnosis processing.

The database 150 refers to a general data structure implemented in a storage space (a hard disk or a memory) of a computer system using a database management program (DBMS) and means a data storage format which freely searches (extracts), deletes, edits, or adds data. The database 150 may be implemented according to the object of the exemplary embodiment of the present disclosure using a relational database management system (RDBMS) such as Oracle, Informix, Sybase, or DB2, an object oriented database management system (OODBMS) such as Gemston, Orion, or O2, and XML native database such as Excelon, Tamino, Sekaiju and has an appropriate field or elements to achieve its own function.

The database 250 according to the exemplary embodiment stores the synthetic model, the virtual patient model, the patient information, the first diagnostic result, and the second diagnostic result and supplies the stored data. The data stored in the database 250 may be various information related to the vascular disease such as the synthetic model, the virtual patient model, the patient information, the first diagnostic result, the second diagnostic result, the biometric authentication information, fractional flow reserve information, and flow feature information.

In the meantime, it is described that the database 250 is implemented in the computing device 200 for diagnosing a vascular disease, but is not necessarily limited thereto and may be implemented as a separate data storage device.

FIG. 3 is a block diagram schematically illustrating a vascular disease diagnosing apparatus according to an exemplary embodiment of the present disclosure.

The vascular disease diagnosing apparatus 300 according to the present disclosure may amplify a quality and a quantity of data for diagnosing a vascular disease by applying the biometric authentication information of the diagnosis subject (patient) and the flow feature information based on the computational fluid dynamics to a machine learning algorithm which is configured by two steps.

A first step algorithm of the machine learning algorithm configured by two steps aims to improve a function of the computational fluid dynamics of the related art.

The first step algorithm of the vascular disease diagnosing apparatus 300 receives a blood vessel shape of a patient acquired from the CT as an input signal, like a fractional flow reserve (FFR) prediction simulator based on the computational fluid analysis technique of the related art and derives the fractional flow reserve (FFR) prediction and the flow feature information including flow factors such as or vorticity or wall shear stress as output signals.

In the first step algorithm of the vascular disease diagnosing apparatus 300, the first learning model is used and the first learning model is trained with a result obtained by analyzing the synthetic model, rather than a blood vessel model of an actual patient, using the computational fluid technique. As a result, in the first step algorithm of the vascular disease diagnosing apparatus 300, the accuracy is similar to an accuracy when the computational fluid technique is used for analysis and the calculation time of the computational fluid technique which is consumed for approximately 10 hours may be shortened to a few minutes.

A second step algorithm of the machine learning algorithm configured by two steps is objected to diagnose a vascular disease by overcoming a limitation of the computational fluid technique.

Because the computational fluid technique does not fully reflect the patient's biometric authentication information, the accuracy may be just approximately 80%. In the present disclosure, in order to improve the diagnosis accuracy, various biometric information (for example, BMI, age, calcium concentration of the blood vessel) which cannot be reflected in the computational fluid technique of the related art needs to be considered. In the second step algorithm, in addition to the fractional flow reserve (FFR) predicted in the first step algorithm, the biometric authentication information of the diagnosis subjects (patients) is received as an input to derive decision making information regarding the diagnosis of the vascular disease or whether to perform a treatment (for example, a medical procedure or a surgery).

The second step algorithm of the vascular disease diagnosing apparatus 300 according to the present disclosure may additionally utilize the biometric authentication information of the diagnosis subject and the flow feature information of a blood flow, as compared with the algorithm of the related art which is simply trained only based on a blood vessel image of the diagnosis subject. Further, the second step algorithm of the vascular disease diagnosing apparatus 300 may supplement the number of data required for learning using the synthetic model.

The vascular disease diagnosing apparatus 300 according to the exemplary embodiment of the present disclosure includes an artificial information acquiring unit 310, a learning model generating unit 320, a patient information acquiring unit 330, a diagnosis processing unit 340, and a result processing unit 350. The vascular disease diagnosing apparatus 300 of FIG. 3 is an example so that all blocks illustrated in FIG. 3 are not essential components and in the other exemplary embodiment, some blocks included in the vascular disease diagnosing apparatus 300 may be added, modified, or omitted. In the meantime, the vascular disease diagnosing apparatus 300 maybe implemented as a computing device which diagnoses a vascular disease and each component included in the vascular disease diagnosing apparatus 300 may be implemented as separate software devices or as a separate hardware device in which the software is combined.

The artificial information acquiring unit 310 acquires a synthetic model and a virtual patient model to generate a learning model for diagnosing a vascular disease. Here, the synthetic model and the virtual patient model may be information which is input by the manipulation of the user or information which is received from an external device. Here, the synthetic model may be a blood vessel image, but is not necessarily limited thereto and may be geometric feature information related to the blood vessel image. Further, the virtual patient model may be patient information about the diagnosis subject which is randomly collected or patient information which is arbitrarily generated for a virtual diagnosis subject.

The learning model generating unit 320 generates a learning model which allows the diagnosis processing unit 340 to diagnose a vascular disease. The learning model generating unit 320 includes a first learning model generating unit 322 and a second learning model generating unit 324.

The first learning model generating unit 322 generates geometric feature parameter learning data based on a predetermined synthetic model and generates a first learning model based on supervised learning using fractional flow reserve data and flow feature data calculated using the shape parameter learning data. Here, the geometric feature parameter learning data includes geometric feature parameters for a top portion, a middle portion, and a bottom portion of the blood vessel of the synthetic model. Here, the geometric feature parameters may include parameters for a length, a curvature, a diameter, eccentricity, etc.

The first learning model generating unit 322 applies the geometric feature parameter learning data, the fractional flow reserve data, and the flow feature data to Gaussian process regression analysis to generate the first learning model. Here, the first learning model is a learning model which allows the diagnosis processing unit 340 to diagnose the vascular disease and performs an operation of receiving the geometric feature parameter information to calculate and output the fractional flow reserve (FFR) information.

The second learning model generating unit 324 acquires biometric authentication data for the virtual patient model and generates a second learning model based on supervised learning using the biometric authentication data, the fractional flow reserve data, and the flow feature data. Here, the fractional flow reserve data refers to data calculated by applying the geometric feature parameter learning data generated based on the virtual patient model to the first learning model and the flow feature data refers to data calculated by applying the geometric feature parameter learning data generated based on the virtual patient model to the computational fluid dynamics CFD.

The second learning model generating unit 324 applies the biometric authentication data, the fractional flow reserve data, and the flow feature data to a support vector machine (SVM) to generate the second learning model. Here, the second learning model is a learning model which allows the diagnosis processing unit 340 to determine whether to perform a surgery on the vascular disease and performs an operation of receiving the biometric authentication data, the fractional flow reserve data, and the flow feature data to calculate and output decision making information about whether to perform a surgery.

The patient information acquiring unit 330 acquires patient information for the diagnosis subject. Here, the patient information may include a blood vessel image of the diagnosis subject and biometric information. Here, the blood vessel image refers to an image obtained by capturing a lesion area and the biometric information may include an age, a gender, a BMI (body mass index), vessel calcification, and hematocrit which may identify the diagnosis subject.

The diagnosis processing unit 340 performs an operation of determining a vascular disease and determining whether to perform a surgery on the vascular disease. The diagnosis processing unit 340 includes a first diagnosis processing unit 342 and a second diagnosis processing unit 344.

The first diagnosis processing unit generates geometric feature parameter information based on the patient information and applies the geometric feature parameter information to the first learning model to calculate the fractional flow reserve (FFR) information. Here, the geometric feature parameter information includes geometric feature parameters for a top portion, a middle portion, and a bottom portion of a blood vessel of the blood vessel image included in the patient information. Here, the geometric feature parameters may include parameters for a length, a curvature, a diameter, eccentricity, etc.

Further, the first diagnosis processing unit 342 applies the geometric feature parameter information to the computational fluid dynamics (CFD) to calculate the flow feature information. Here, the computational fluid dynamics (CDF) discretizes the Navier-strokes equations which is a non-linear partial differential equation describing a fluid phenomenon, using methods such as a finite difference method (FDM), a finite element method (FEM), and a finite volume method (FVM), to convert the Navier-strokes equations into algebraic equations and calculate a fluid flow problem using an algorithm of numerical methods. The first diagnosis processing unit 342 calculates the flow feature information including vorticity, a wall shear stress, a pressure, a velocity, WSS, OSI, and APS. The first diagnosis processing unit 342 transmits the calculated fractional flow reserve (FFR) information and flow feature information to the second diagnosis processing unit 344. In the meantime, the first diagnosis processing unit 342 transmits the calculated fractional flow reserve (FFR) information to a first result processing unit 352 to be output.

The second diagnosis processing unit 344 acquires the biometric authentication information included in the patient information and acquires the fractional flow reserve (FFR) information and the flow feature information from the first diagnosis processing unit 342.

The second diagnosis processing unit 344 applies the biometric authentication information, the fractional flow reserve information, and the flow feature information to the second learning model to diagnose the vascular disease and determine whether to perform the surgery on the vascular disease.

The second diagnosis processing unit 344 analyzes a stenosis state of the blood vessel based on the second learning model and determines whether to perform the surgery on the vascular disease based on the stenosis state.

The second diagnosis processing unit 344 receives the biometric authentication information, the fractional flow reserve information, and the flow feature information to calculate decision making information about whether to perform the surgery. Here, the decision making information may be configured by binary numbers. For example, if the decision making information is "0", the vascular disease diagnosing apparatus 300 proposes another treatment without performing the surgery on the vascular disease. If the decision making information is "1", the vascular disease diagnosing apparatus 300 proposes to immediately perform the surgery on the vascular disease.

The result processing unit 350 performs an operation of outputting a diagnostic result of the diagnosis processing unit 340. The result processing unit 350 includes a first result processing unit 352 and a second result processing unit 354. The first result processing unit 350 receives and outputs the fractional flow reserve (FFR) information calculated by the first diagnosis processing unit 342. Even though it is described that the first result processing unit 350 outputs only the fractional flow reserve (FFR) information, the present disclosure is not limited thereto and the first result processing unit 350 may further output the flow feature information.

The second result processing unit 354 receives and outputs the decision making information about whether to perform the surgery calculated by the second diagnosis processing unit 344. Even though it is described that the second result processing unit 354 outputs only the decision making information, the present disclosure is not limited thereto and may further output the biometric authentication information, the fractional flow reserve information, and the flow feature information which are used by the second diagnosis processing unit 344 to calculate the decision making information.

FIGS. 4A and 4B are flow charts for explaining an operation of generating a learning model for diagnosing a vascular disease according to an exemplary embodiment of the present disclosure. Referring to FIG. 4A, the vascular disease diagnosing apparatus 300 acquires a synthetic model and virtual patient information (artificial information) in step S402.

The vascular disease diagnosing apparatus 300 generates a first learning model based on the synthetic model in step S404.

The vascular disease diagnosing apparatus 300 generates a second learning model based on the virtual patient information and the first learning model in step S406.

FIG. 4B illustrates a detailed operation of generating the first learning model and the second learning model in the vascular disease diagnosing apparatus 300.

Hereinafter, an operation of generating the first learning model in the first learning model generating unit 322 will be described (STEP 1).

The first learning model generating unit 322 acquires a predetermined synthetic model in step S410 and generates geometric feature parameter learning data based on the synthetic model in step S412. Here, the geometric feature parameter learning data includes geometric feature parameters for a top portion, a middle portion, and a bottom portion of a blood vessel of the synthetic model. Here, the geometric feature parameters may include parameters for a length, a curvature, a diameter, eccentricity, etc.

The first learning model generating unit 322 performs the computational fluid dynamics (CFD) based on the geometric feature parameter learning data in step S420 to calculate the fractional flow reserve data and the flow feature data in steps S422 and S424.

The first learning model generating unit 322 is trained for Gaussian process regression analysis with the geometric feature parameter learning data, the fractional flow reserve data, and the flow characteristic data as inputs to generate the first learning model 400 in step S430.

Hereinafter, an operation of generating the second learning model in the second learning model generating unit 324 will be described (STEP 2).

The second learning model generating unit 324 acquires a virtual patient model in step S440 and generates geometric feature parameter learning data for the virtual patient model in step S450. Here, the geometric feature parameter learning data includes geometric feature parameters for a top portion, a middle portion, and a bottom portion of the blood vessel image included in the virtual patient model. The shape parameters may include parameters for a length, a curvature, a diameter, eccentricity, etc.

The second learning model generating unit 324 applies the geometric feature parameter learning data to the first learning model 400 to calculate the fractional flow reserve data insteps S460 and 462.

The second learning model generating unit 324 applies the geometric feature parameter learning data to the computational fluid dynamics (CFD) to calculate the flow feature data in steps S470 and S472, The second learning model generating unit 324 acquires biometric authentication information included in the virtual patient model in step S480.

The second learning model generating unit 324 applies the biometric authentication data, the fractional flow reserve data, and the flow feature data as inputs to a support vector machine (SVM) to generate the second learning model 402 in step S490.

Even though in FIGS. 4A and 4B, it is described that the steps are sequentially executed, the present disclosure is not necessarily limited thereto. In other words, the steps described in FIGS. 4A and 4B may be modified to be executed or one or more steps may be executed in parallel so that FIGS. 4A and 4B are not limited to a time-sequential order.

The learning model generating method for diagnosing a vascular disease according to the exemplary embodiment described in FIGS. 4A and 4B may be implemented by an application (or a program) and may be recorded in a terminal device (or computer) readable recording medium. The recording medium which has the application (or program) for implementing the learning model generating method according to the exemplary embodiment for diagnosing the vascular disease recorded therein and is readable by the terminal device (or a computer) includes all kinds of recording devices or media in which computing system readable data is stored.

FIGS. 5A and 5B are flowcharts for explaining an operation of generating a first learning model and a second learning model according to an exemplary embodiment of the present disclosure. FIG. 5A illustrates an operation of generating a first learning model and FIG. 5B illustrates an operation of generating a second learning model.

Referring to FIG. 5A, the vascular disease diagnosing apparatus 300 acquires an artificial blood vessel geometric feature parameter Gs and computational fluid analysis data $D_{CFD}$ in steps S510 and S512. Here, the artificial blood vessel geometric feature parameter $G_S$ may be fractional flow reserve data and the computational fluid analysis data $D_{CFD}$ maybe flow feature data.

The vascular disease diagnosing apparatus 300 generates data samples $G_S$ and $D_{CFD}$ based on the artificial blood vessel geometric feature parameter Gs and computational fluid analysis data $D_{CFD}$ in step S520.

The vascular disease diagnosing apparatus 300 generates learning data X and Y and test data X' and Y' based on the data samples $G_S$ and $D_{CFD}$ in steps S530 and S532 and performs the Gaussian process regression learning using the learning data X and Y in step S540.

The vascular disease diagnosing apparatus 300 performs a test and a feedback for repeated learning in step S550 and generates the first learning model based thereon in step S552. Referring to FIG. 5B, the vascular disease diagnosing apparatus 300 acquires a patient blood vessel geometric feature parameter $G_P$, patient biometric information $B_P$, and a patient FFR measurement value $FFR_P$ in step S560.

The vascular disease diagnosing apparatus 300 generates data samples $G_S$ and $B_P$ based on the patient blood vessel geometric feature parameter $G_P$, the patient biometric information $B_P$, and the patient FFR measurement value $FFR_P$ in step S570.

The vascular disease diagnosing apparatus 300 generates learning data X and Y and test data X' and Y' based on the data samples $G_S$ and $B_P$ in steps S572 and S574 and performs the support vector machine (SVM) learning using the learning data X and Y in step S580.

The vascular disease diagnosing apparatus 300 performs a test and a feedback for repeated learning in step S590 and generates the second learning model based thereon in step S592. FIGS. 6A and 6B are flow charts for explaining a method for diagnosing a vascular disease according to an exemplary embodiment of the present disclosure.

Referring to FIG. 6A, the vascular disease diagnosing apparatus 300 acquires patient information in step S602.

The vascular disease diagnosing apparatus 300 performs a first diagnosis processing using the geometric feature parameter information generated based on the patient information in step S604.

The vascular disease diagnosing apparatus 300 outputs a first diagnostic result for the first diagnosis processing in step S606. Here, the first diagnostic result may be at least one of the fractional flow reserve (FFR) information and the flow feature information.

The vascular disease diagnosing apparatus 300 performs a second diagnosis processing using the first diagnostic result and the biometric authentication information included in the patient information.

The vascular disease diagnosing apparatus 300 outputs a second diagnostic result for the second diagnosis processing in step S609. Here, the second diagnostic result may include information about whether to perform the surgery on the vascular disease.

FIG. 6B illustrates a detailed operation of performing the first diagnosis processing and the second diagnosis processing in the vascular disease diagnosing apparatus 300.

Hereinafter, an operation of performing the first diagnosis processing in the first diagnosis processing unit 342 will be described (STEP 1).

The first diagnosis processing unit 342 acquires patient information in step S610 and generates geometric feature parameter information based on the patient information in step S620. Here, the geometric feature parameter information includes shape parameters for a top portion, a middle portion, and a bottom portion of a blood vessel of the blood vessel image included in the patient information. The geometric feature parameters may include parameters for a length, a curvature, a diameter, eccentricity, etc.

The first diagnosis processing unit 342 applies the generated geometric feature parameter information to the first learning model 400 to calculate the fractional flow reserve (FFR) information in steps S630 and S640.

The first diagnosis processing unit 342 outputs the calculated fractional flow reserve (FFR) information as a first diagnostic result in step S642.

The first diagnosis processing unit 342 applies the generated geometric feature parameter information to the computational fluid dynamics (CFD) to calculate the flow feature information in steps S650 and 652. Here, the flow feature information may include information about vorticity, a wall stress, a pressure, a velocity, WSS, OSI, and APS.

Hereinafter, an operation of performing the second diagnosis processing in the second diagnosis processing unit 344 will be described (STEP 2).

The second diagnosis processing unit 344 acquires the biometric authentication information included in the patient information in step S660 and acquires the fractional flow reserve (FFR) information and the flow feature information from the first diagnosis processing unit.

The second diagnosis processing unit 344 applies the biometric authentication information, the fractional flow reserve information, and the flow feature information to the second learning model 402 to calculate and output a second diagnostic result in steps S680 and 690. The second diagnosis processing unit 344 applies the biometric authentication information, the fractional flow reserve information, and the flow feature information to the second learning model 402 to diagnose the vascular disease and determine whether to perform the surgery on the vascular disease.

Even though in FIGS. 6A and 6B, it is described that the steps are sequentially executed, the present disclosure is not necessarily limited thereto. In other words, the steps described in FIGS. 6A and 6B may be modified to be executed or one or more steps may be executed in parallel so that FIGS. 6A and 6B are not limited to a time-sequential order.

The vascular disease diagnosing method according to the exemplary embodiment described in FIGS. 6A and 6B may be implemented by an application (or a program) and may be recorded in a terminal (or computer) readable recording media. The recording medium which has the application (or program) for implementing the vascular disease diagnosing method according to the exemplary embodiment recorded therein and is readable by the terminal device (or a computer) includes all kinds of recording devices or media in which computing system readable data is stored.

FIG. 7A and 7B are an exemplary view illustrating a diagnostic result of a vascular disease according to an exemplary embodiment of the present disclosure and a diagnostic result of a vascular disease according to the related art.

FIG. 7A illustrates a diagnostic result calculated by a diagnosing method ($FFR_{EXP}/DEC_{EXP}$) of the related art and a diagnostic result calculated by a diagnosing method ($FFR_{GPR}/DEC_{GPR}$) of the present disclosure, for a plurality of patients.

Referring to FIG. 7A, it is confirmed that the diagnostic results for 11 patients out of a total of 20 patients match the diagnosing method ($FFR_{GPR}/DEC_{SVM}$) of the present disclosure and the diagnosing method ($FFR_{EXP}/DEC_{EXP}$) of the related art.

It is further confirmed that the diagnostic results for 4 patients out of a total of 20 patients match only the diagnosing method ($DEC_{SVM}$) of the present disclosure and the diagnostic results for 2 patients out of a total of 20 patients match only the diagnosing method ($FFR_{GPR}$) of the present disclosure.

It is confirmed that the diagnostic results for 3 patients out of a total of 20 patients do not match the diagnosing method ($FFR_{GPR}/DEC_{SVM}$) of the present disclosure and the diagnosing method ($FFR_{EXP}/DEC_{EXP}$) of the related art.

FIG. 7B illustrates a result of comparing the accuracy, the sensitivity, and the specificity of the present disclosure and the related art.

In FIG. 7B, the accuracy may be calculated by "accurately predicted data/all data, the sensitivity is calculated by "the number of patients who require the surgery/accurately predicted data", and the specificity is calculated by "the number of patients who do not require the surgery/accurately predicted data".

FIGS. 8 and 9 are exemplary views for explaining an operation of a vascular disease system according to an exemplary embodiment of the present disclosure.

Referring to FIG. 8, a vascular disease system may determine a vascular disease and whether to perform a surgery by the following order:

step S810: perform non-invasive diagnosis step S820: input or acquire vessel parameters, blood parameters, and other parameters (input FFR related parameters)

step S830: transmit data using a terminal of a diagnostician (doctor)

step S840: calculate and estimate a vascular disease by the diagnosis processing using functional machine learning (a first learning model and a second learning model)

step S850: output a diagnostic result using an augmented reality or virtual reality device which interworks with the terminal of the diagnostician (doctor)

step S860: provide clear guideline for decision making in the form of "yes" or "no" regarding whether to perform a surgery, based on the diagnostic result and additionally provide the fractional flow reserve (FFR) and other parameters (a pressure, a velocity, WSS, OSI, and APS).

Referring to FIG. 9, a vascular disease system may determine a vascular disease and whether to perform a surgery by the following order to cure the vascular disease:

step S910: perform non-invasive diagnosis in an operating room step S920: a diagnostician (doctor) transmits data to a vascular disease diagnosing apparatus through a terminal step S930: perform simulation/machine learning based analysis in the vascular disease diagnosing apparatus step S940: the diagnostician (doctor) receives data for the diagnostic result by the terminal step S950: check the diagnostic result to immediately determine whether to perform a surgery by the diagnostician (doctor)

The vascular disease system allows the diagnosis subject (patient) and the diagnostician (doctor) to wait only for less than one hour at a predetermined site (a doctor's office or an operating room) to determine whether to perform the surgery so that the diagnosis and the treatment can be quickly performed.

It will be appreciated that various exemplary embodiments of the present disclosure have been described herein for purposes of illustration, and that various modifications and changes may be made by those skilled in the art without departing from the scope and spirit of the present disclosure. Accordingly, the exemplary embodiments of the present disclosure are not intended to limit, but describe the technical spirit of the present disclosure and the scope of the technical spirit of the present disclosure is not restricted by the exemplary embodiments. The protective scope of the exemplary embodiment of the present disclosure should be construed based on the following claims, and all the technical concepts in the equivalent scope thereof should be construed as falling within the scope of the exemplary embodiment of the present disclosure.

What is claimed is:

1. A vascular disease diagnosing method for diagnosing a vascular disease by a vascular disease diagnosing apparatus, the method comprising:
generating first geometric feature parameter learning data based on a predetermined synthetic model;
calculating first fractional flow reserve data and first flow feature data using the first geometric feature parameter learning data;
applying the first geometric parameter learning data, the first fractional flow reserve data, and the first flow feature data to Gaussian process regression analysis to generate a first learning model;
acquiring virtual biometric authentication data for a virtual patient model;
generating second geometric feature parameter learning data based on the virtual patient model;
applying the second geometric feature parameter learning data to the first learning model to obtain second fractional flow reserve data;
applying the second geometric feature parameter learning data to computational fluid dynamics (CFD) to obtain second flow feature data;
generating a second learning model based on the virtual biometric authentication data, the second fractional flow reserve data, the second flow feature data, information related to determining of a vascular disease, and information regarding whether to perform a surgery on the vascular disease;
acquiring patient information for a diagnosis subject;
generating geometric feature parameter information based on the patient information;
applying the geometric feature parameter information to the first learning model to calculate fractional flow reserve (FFR) information;
applying the geometric feature parameter information to computational fluid dynamics (CFD) to calculate flow feature information;
acquiring biometric authentication information of the diagnosis subject included in the patient information; and
applying the fractional flow reserve information, the flow feature information, and the biometric authentication information of the diagnosis subject to the second learning model to determine a vascular disease and determine whether to perform a surgery on the vascular disease.

2. The vascular disease diagnosing method according to claim 1, wherein the second learning model is a model generated by applying the biometric authentication data, the second fractional flow reserve data, the second flow feature data, information related to determining of a vascular disease, and information regarding whether to perform a surgery on the vascular disease to a support vector machine (SVM).

3. The vascular disease diagnosing method according to claim 1, wherein a stenosis state of a blood vessel is analyzed based on the second learning model and whether to perform a surgery on the vascular disease is determined based on the stenosis state.

4. A computer program stored in a non-transitory recording medium wherein when the program is executed by a computer, the computer performs the vascular disease diagnosing method according to claim 1.

5. The vascular disease diagnosing method according to claim 1, wherein the flow feature information includes vorticity.

6. The vascular disease diagnosing method according to claim 1, wherein the virtual patient model includes patient information arbitrarily generated for a virtual diagnosis subject.

7. The vascular disease diagnosing method according to claim 1, wherein the synthetic model includes a blood vessel image.

8. A vascular disease diagnosing apparatus, comprising:
one or more processors; and
a memory in which one or more programs executed by the one or more processors are stored,
wherein when the programs are executed by the one or more processors, the one or more processors perform operations including:
generating first geometric feature parameter learning data based on a predetermined synthetic model;
calculating first fractional flow reserve data and first flow feature data using the first geometric feature parameter learning data;
applying the first geometric parameter learning data, the first fractional flow reserve data, and the first flow feature data to Gaussian process regression analysis to generate a first learning model;
acquiring virtual biometric authentication data for a virtual patient model;
generating second geometric feature parameter learning data based on the virtual patient model;
applying the second geometric feature parameter learning data to the first learning model to obtain second fractional flow reserve data;
applying the second geometric feature parameter learning data to computational fluid dynamics (CFD) to obtain second flow feature data;
generating a second learning model based on the virtual biometric authentication data, the second fractional flow reserve data, the second flow feature data, information related to determining of a vascular disease, and information regarding whether to perform a surgery on the vascular disease;
acquiring patient information for a diagnosis subject;
generating geometric feature parameter information based on the patient information;
applying the geometric feature parameter information to the first learning model to calculate fractional flow reserve (FFR) information;
applying the geometric feature parameter information to computational fluid dynamics (CFD) to calculate flow feature information;
acquiring biometric authentication information of the diagnosis subject included in the patient information; and
applying the fractional flow reserve information, the flow feature information, and the biometric authentication information of the diagnosis subject to the second learning model to determine a vascular disease and determine whether to perform a surgery on the vascular disease.

* * * * *